United States Patent
Ouwerkerk

(10) Patent No.: US 12,156,744 B2
(45) Date of Patent: Dec. 3, 2024

(54) TAILORABLE SENSOR DEVICE FOR PHYSIOLOGICAL PARAMETER SENSING

(71) Applicant: KONINKLIJKE PHILIPS N.V., Eindhoven (NL)

(72) Inventor: Martin Ouwerkerk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1574 days.

(21) Appl. No.: 14/360,045

(22) PCT Filed: Nov. 11, 2012

(86) PCT No.: PCT/IB2012/056420
§ 371 (c)(1),
(2) Date: May 22, 2014

(87) PCT Pub. No.: WO2013/080075
PCT Pub. Date: Jun. 6, 2013

(65) Prior Publication Data
US 2014/0323840 A1    Oct. 30, 2014

Related U.S. Application Data

(60) Provisional application No. 61/564,366, filed on Nov. 29, 2011.

(51) Int. Cl.
*A61B 5/00* (2006.01)
*A61B 5/05* (2021.01)
*A61B 5/0531* (2021.01)

(52) U.S. Cl.
CPC ............ *A61B 5/684* (2013.01); *A61B 5/0531* (2013.01); *A61B 5/681* (2013.01); *A61B 5/72* (2013.01); *A61B 5/7475* (2013.01)

(58) Field of Classification Search
CPC ..... A61B 5/681; A61B 5/02438; A61B 5/024; A61B 5/742; A61B 5/6824; A61B 5/6831;
(Continued)

(56) References Cited

U.S. PATENT DOCUMENTS 4,295,472 A * 10/1981 Adams .................. A61B 5/024
                                                600/503
4,847,729 A *  7/1989 Hee .......................... A61N 1/14
                                                224/175
(Continued)

FOREIGN PATENT DOCUMENTS

DE     102008013731 B3    9/2009
EP          2196144 A1    6/2010
(Continued)

OTHER PUBLICATIONS

Westerink, J. et al., "Emotion Measurement Platform for Daily Life Situations", . IEEE, vol. 978, No. 1, pp. 4244-4799, 2009.

*Primary Examiner* — Joseph A Stoklosa
*Assistant Examiner* — Brian M Antiskay

(57) ABSTRACT

A sensor device and method for tightening and positioning the sensor device with a wristband or strap (62) for a range of wrist sizes and shapes or other body portions, such that the optimal sensor position is obtained and maintained during ambulatory use, which provides two-sided fastening of the strap (62). The strap (62) has a marker (67) that is positioned by the wearer at a predetermined measuring position, e.g., on the middle of the volar side of the wrist. The wrist is then put on the table to fix its position, and the strap (62) is tightened on both sides of the wrist. This ensures a precision of at least 5 mm of the position of the sensors (66) in the strap.

16 Claims, 3 Drawing Sheets

(58) Field of Classification Search
CPC . A61B 5/02405; A61B 5/0402; A61B 5/6804; A61B 5/6802; A61B 5/0404; G08B 21/0453
USPC .................................. 600/372–395, 508–509
See application file for complete search history.

(56) References Cited

U.S. PATENT DOCUMENTS

| | | |
|---|---|---|
| 6,272,836 B1 * | 8/2001 | Fat ..................................... 59/80 |
| 2005/0177051 A1 * | 8/2005 | Almen .......................... 600/509 |
| 2005/0234351 A1 | 10/2005 | Nishii |
| 2007/0191718 A1 | 8/2007 | Nakamura |
| 2009/0048526 A1 * | 2/2009 | Aarts ................... A61B 5/0245 600/384 |
| 2009/0143689 A1 * | 6/2009 | Berry et al. .................. 600/508 |
| 2009/0168612 A1 | 7/2009 | Robin |
| 2010/0076331 A1 * | 3/2010 | Chan ...................... A61B 5/681 600/509 |
| 2010/0268056 A1 * | 10/2010 | Picard et al. ................. 600/388 |

FOREIGN PATENT DOCUMENTS

| | | |
|---|---|---|
| EP | 2316298 A1 | 5/2011 |
| FR | 2685189 A1 | 6/1993 |
| JP | 61121115 | 7/1986 |
| JP | 2002369806 A | 12/2002 |
| JP | 2003144209 | 5/2003 |
| JP | 2010220948 A | 10/2010 |
| WO | WO9012519 A1 | 11/1990 |

\* cited by examiner

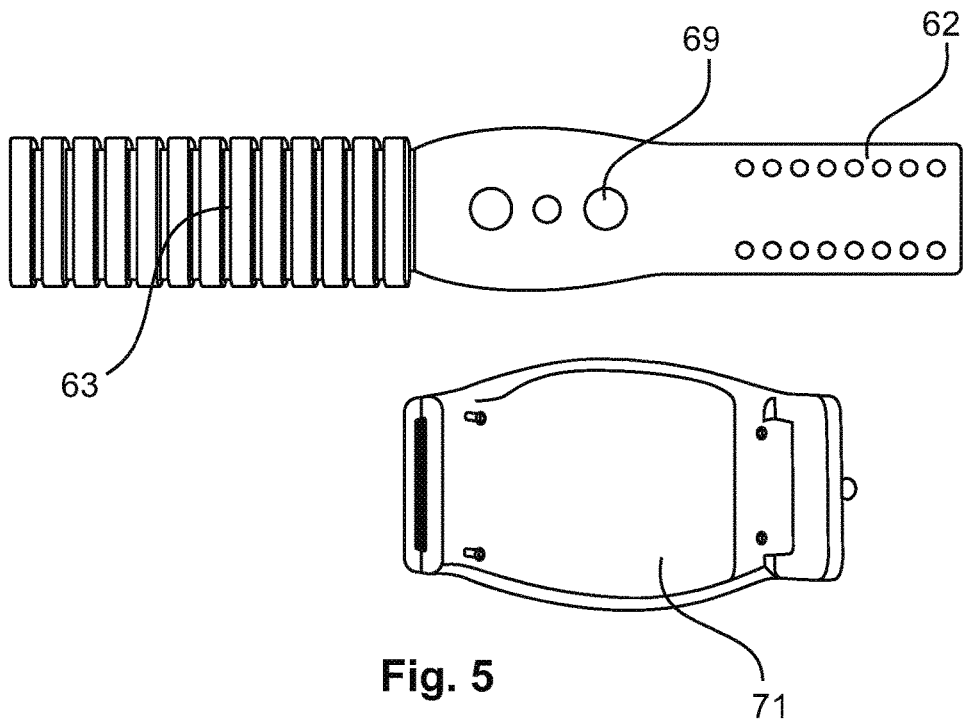

Fig. 5

| S110 - the sensor electrodes are put at an optimal position of the volar side of the wrist, |

↓

| S120 - the two sides or ends of the wrist strap are wrapped around the wrist, and the signal processing unit of the sensor device is put on top of the wrist |

↓

| S130 - the optimal size of the wrist strap for this person is marked |

↓

| S140 - the excess material is removed from the wristband |

↓

| S150 - On one side the wrist strap is inserted and fixed in the signal processing unit |

↓

| S160 - the other side of the wrist strap is fixed onto one or two knobs of the knob-based fixing mechanism after putting the device on the wrist |

Fig. 6

TAILORABLE SENSOR DEVICE FOR PHYSIOLOGICAL PARAMETER SENSING

FIELD OF THE INVENTION

The present invention relates to a sensor device and method of tightening and positioning the sensor device to a body portion of a patient.

BACKGROUND OF THE INVENTION

Psychophysiological parameter sensing at the wrist for mental and physical health status assessment, as described for example in Westerink, J. et al.: "Emotion measurement platform for daily life situations" (2009), is highly dependent on a correct and stable positioning of the sensor. Within the human population the wrist circumference and shape varies by a large margin, making one-size-fits-all sensor strap devices, such as sensor wristbands, impossible to make. As an example, skin conductance sensor wristbands may comprise discrete tension indicators, vitality bracelets, Q-sensors or the like.

However, at the volar side of the wrist the skin conductance is lower than at the standard position on the palm of the hand. For blood volume pulse measurements at the volar side of the wrist the optimal position for the light source and photo detector is in the proximity of an artery. The wrist circumference and shape distribution for the human population spans a large scope. A wristband sensor device therefore cannot be a one-size-fits all, but needs expert positioning at the optimal locations and tailoring the size and shape of the wristband. This is too expensive and complex for a mainstream product.

SUMMARY OF THE INVENTION

An object of the present invention is to provide a strap-based sensor device which can be easily and effectively tailored to individual needs of the patient.

This object is achieved by a sensor device as claimed in claim 1 and by a fastening method as claimed in claim 11.

Accordingly, a single strap with integrated sensor(s) can be adjustably fixed to the signal processing unit at both ends. This ensures high precision of the position of the sensor(s) in the wristband with respect to the measuring position at the body.

According to a first aspect, the signal processing unit may comprise a user interface, so that a user or patient wearing the sensor device can monitor and/or control measuring or sensor functions.

According to a second aspect which can be combined with the first aspect, the signal processing unit may comprise a data storage for storing measuring results. Thereby, measuring results can be monitored and stored for later evaluation or assessment of measuring trends.

According to a third aspect which can be combined with the first or second aspect, the strap may comprise at least one marker for positioning the at least one sensor at a predetermined measuring position of a wrist of the body. This facilitates correct positioning and tightening of the strap of the sensor device. According to an exemplary implementation, the predetermined measuring position may be located at the thumb side of the volar side of the wrist.

According to a fourth aspect which can be combined with any one of the first to third aspects, the strap may be adapted to be tightened at both sides of a wrist of the body by the adjustable fastening. This two-sided tightening option ensures correct placement of the electrode(s) and tight but comfortable fit of the strap.

According to a fifth aspect which can be combined with any one of the first to fourth aspects, the strap may be adapted to be inserted in the signal processing unit at one end of the strap and to be adjustably fixed onto a knob portion at the other end of the strap. These fixation options provide easy handling during positioning and tightening of the sensor device.

According to a sixth aspect which can be combined with any one of the first to fifth aspects, the one end of the strap may comprise a segmented portion with a predetermined segmented pattern for removing or adding strap pieces. The segmented pattern facilitates length adjustment of the strap by providing predetermined cutting segments. The segments may be arranged as a cutting pattern, from which strap pieces can be cut away, or may be already separated from one another and can be added or removed piece by piece.

According to a seventh aspect which can be combined with any one of the first to sixth aspects, the strap may comprise at least one recess for accommodating the at least one electrode. Thereby, replacement of a sensor (e.g. electrode) can be facilitated by simply pressing it into the recess.

Further advantageous embodiments are defined below.

BRIEF DESCRIPTION OF THE DRAWINGS

The invention will now be described, by way of example, based on embodiments with reference to the accompanying drawings, wherein:

FIG. 5 shows a perspective view of a sensor device with a user interface according the second embodiment after positioning and tightening at a human wrist; and FIG. 6 shows a flow diagram of a procedure for positioning and tightening the sensor device according to the second embodiment.

DESCRIPTION OF PREFERRED EMBODIMENTS

Various embodiments of the present invention will now be described based on a monitoring or sensor device for measuring skin conductance at a wrist of a human or animal patient. Of course, the present invention can be used for measuring other physiological or psychophysiological parameter(s) at the same or other portions of the body. It is clear to the skilled person that the sensor device and particularly the strap can be adapted to the size and shape of other body portions where a desired parameter can be measured.

The sensor device with its electrodes can be positioned and tightened to the patient and monitors the skin conductance of the patient. The skin conductance measurements can be used e.g. for determining if a patient is in a condition where ventilation may or should be changed or for determining if the change of ventilation has been successful. Of course, use for other applications and other measuring parameters is possible as well.

Figure 1:
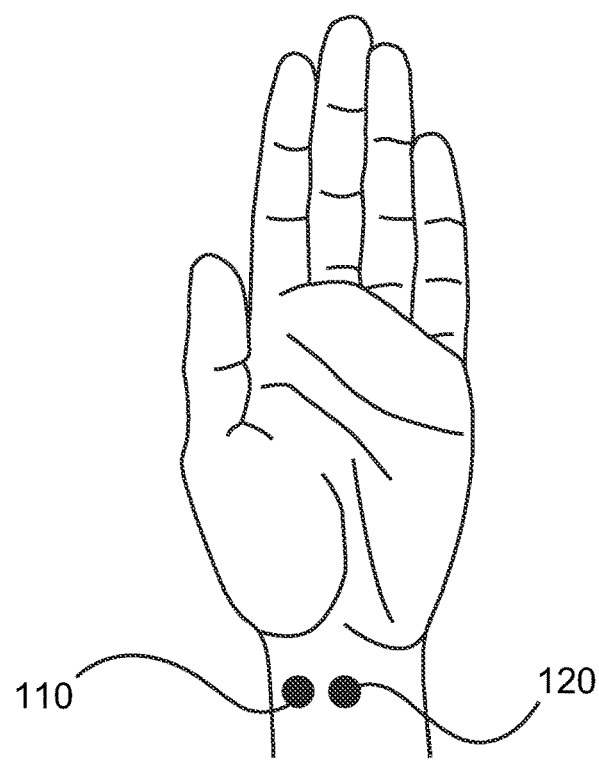
FIG. 1 shows a schematic wrist of a patient with optimum positions for measuring electrodes.

FIG. 1 shows a schematic hand of a patient with preferred locations of measuring electrodes. In FIG. 1, a left hand is shown, but the same method of positioning applies for the right hand as well in a mirrored fashion. The quality of the skin conductance signal depends largely on the locations where the electrodes are placed. At the volar side of the wrist the skin conductance is lower than at the standard position on the palm of the hand. When studying the skin conductance as a function of the exact location at the volar side of the wrist a large variation is found. Optimal is the region at the thumb side of the volar side of the wrist. The central region shows intermediate values of skin conductance, whereas the side of the little finger gives the lowest skin conductance values. Since two electrodes are needed with a diameter of about 1 cm, and a wide wristband is undesirable, the optimal measuring positions 110, 120 are shown in FIG. 1.

More specifically, a location to obtain the best signal is on the wrist, with one electrode on the line in the middle of the volar side of the wrist, at a distance of about 3-5 cm from the hand and the other electrode is positioned next to the first electrode perpendicular to this line on the side of the thumb. An optimal distance between the electrodes is 5 mm, with a minimum of 1 mm, and a maximum of 10 mm. This distance is measured from the outer edges of the electrodes at the measuring positions 110, 112. Thus, in an exemplary case the electrodes may have a standard diameter of about 15 mm. Then, the spacing or distance between the centers of the electrodes may be about 20 mm.

In another embodiment, a ground electrode can be placed anywhere along the strap and preferably be much larger than the active electrode. The active electrode preferably is circular, may have a diameter of 1 cm and can be placed 2 cm from the center of the volar side of the wrist at the side of the thumb. As another option, the ground electrode may consist of conductive cloth covering a large portion of the inside of the strap.

The skin conductance can be measured by measuring the voltage drop over the two electrodes in a serial circuit containing a stable reference voltage source, a reference resistance which should be stable to thermal fluctuations, and the human skin contacted by the electrodes made of a conductive and skin compatible or non-irritant or non allergic material capable of bridging the electronic/ionic interface without or with little capacitive or resistive interference. The electrodes may be standard skin conductance electrodes as used by skin conductance experts.

As another option, the measured skin conductance could be combined with other physiological parameters (such as $SpO_2$, $P_{et}CO_2$, respiration rate, respiration rate variability, et cetera) and/or ventilator settings to give a final advice or indication or control output. The final advice can be in the form of a numerical value (e.g. 1 (e.g. relaxed) to 10 (e.g. serious discomfort)), a traffic light color (red-yellow/orange-green), or output instruction message like "ready for extubation", "stop the SBT", "start an STB", "reduce ventilation" or "increase ventilation". Of course, this is likely to be only one of the possible usages. An alternative focus could be put on stress at work, and the prevention of prolonged stress related ailments, such as burnout, adrenal fatigue. A further usage could be aggression prevention for psychiatric patients, where the device offers an early warning of rising anger.

Figure 2:
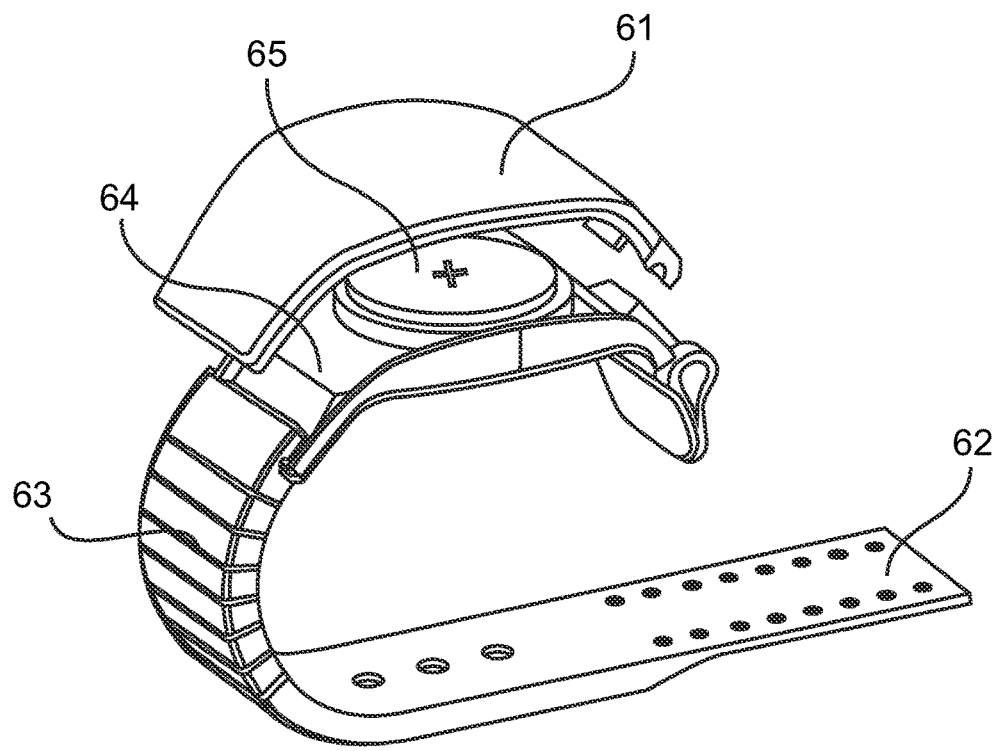
FIG. 2 shows a perspective view of a sensor device according to a first embodiment with lifted upper housing portion.

FIG. 2 shows a strap-based implementation of the sensor device with lifted upper housing or coverage. In order to position the electrodes on the above mentioned desired places or measuring positions of the wrist, a strap 62 as depicted in FIG. 2 could be used. This strap 62 contains the two electrodes (not shown) and has a length that is adjustable at two different places at both ends. From one side an appropriate number of segments is removed from a segmented portion 63 (e.g. by cutting away) to position the skin conductance sensor electrodes at the positions of FIG. 1, and from the other side of the strap the excess part next to the most optimal hole is cut off to fit the strap to the wrist of a person, such that the skin conductance electrodes are in a firm, but comfortable position, fully touching the skin of the volar side of the wrist. Thus, a procedure for tightening and positioning a sensor wristband for a range of wrist sizes and shapes can be provided, wherein the two-sided fastening of the strap ensures an optimal electrode or sensor position which is maintained during ambulatory use. As an alternative option, the segments of the segmented portion 63

The skin conductance can be measured by measuring the voltage drop over the two electrodes in a serial circuit containing a stable reference voltage generated from a voltage source 65 (e.g. battery) of preferably 1.2V (but not more than 5V), a reference resistance of typical 3.3 MΩ or 10 MΩ, and the human skin contacted by the two electrodes made of a conductive material, having a diameter of 1 cm. The electrical circuit or connections may be provided on a flexible circuit foil 64 and may be protected by the coverage on which a user interface 61 may be arranged. The voltage is amplified and digitized by an analogue to digital converter (not shown) with e.g. 12 to 16 bit precision, using a stable reference voltage of 3.0V.

Figure 3:
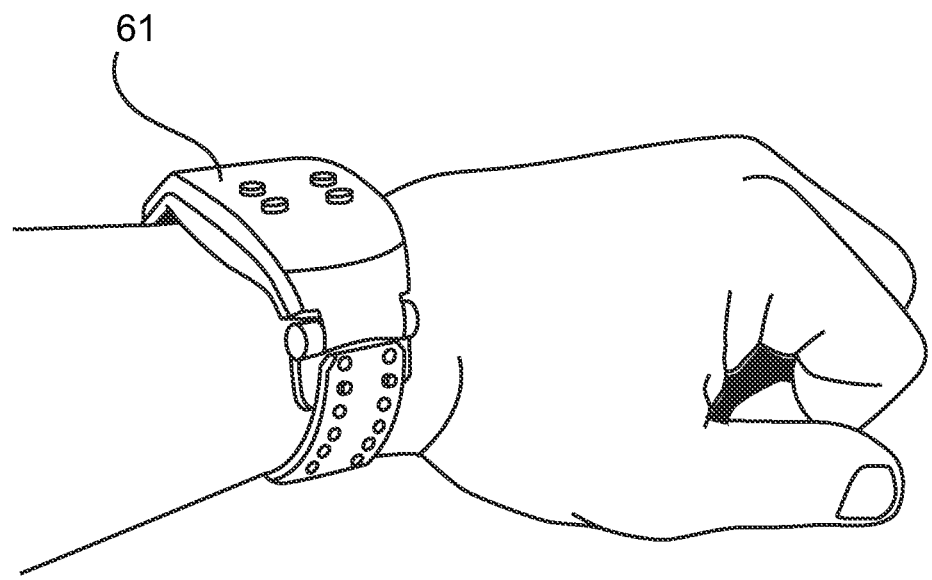
FIG. 3 shows a bottom view of a signal processing unit and separated sensor strap of a sensor device according a second embodiment prior to positioning and tightening.
Figure 4:
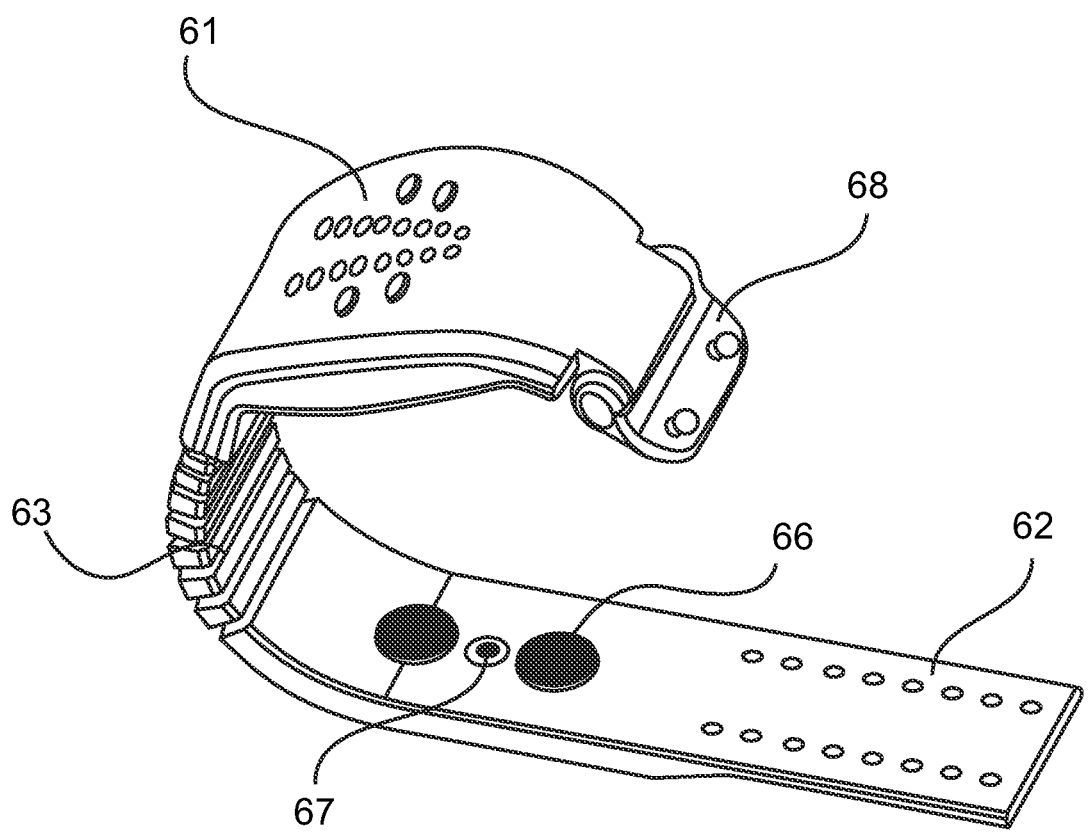
FIG. 4 shows a perspective view of a sensor device with a user interface according the second embodiment.

FIG. 3 shows a bottom view of a second embodiment with non-adjusted wrist strap 62 with the segmented pattern 63 at one end and one or two series of fixing holes at the other end, and a signal processing unit 71 which may comprise a user interface and data storage or memory. Furthermore, recesses 69 are provided in the wrist strap 62 for accommodating sensing electrodes. The wrist strap 62 may be made of rubber with a hollow tunnel for electronic wiring between the sensing electrodes and signal processing unit 71 with its user interface and data storage. FIG. 4 shows a perspective view of the sensor device according to the second embodiment, where the user interface 61 with its control elements (e.g. mechanical, optical and/or audio indication and/or control elements or the like) is shown. Furthermore a knob-based fixing mechanism 68 is mounted to the signal processing unit 71 which can be fixed to one pair of the holes provided in the wrist strap 62. Additionally, the wrist strap 62 has a marker 67 that is positioned by the wearer on the middle of the volar side of the wrist. The wrist may then be put on the table to fix its position, and the strap is tightened on both sides of the wrist by the two-sided fixing mechanism with the segmented pattern 63 and the holes of the wrist strap 62. This ensures a precision of at least 5 mm of the position of the sensors 66 in the wrist strap 62. Improvement could be achieved by providing a table of wrist circumferences and a recommended number of segments to cut or remove from the strap 62. As an alternative option, the segments of the segmented portion 63 may be already separated from one another and can be added or removed piece by piece.

FIG. 5 shows a perspective view of the sensor device according to the second embodiment after positioning and tightening at the wrist. As can be gathered from FIG. 5, one end of the wrist strap 62 is fixed with the knobs of the knob-based fixing mechanism 68. Of course, other adaptive fixing mechanism with clamping, flip locking, or other locking mechanisms could be used for fixing the wrist strap 62 to the signal processing unit 71. An additional stretching function of the strap 62 may help to provide good fit. To achieve this, an elastic band may be provided in a tunnel of the strap 62, which can be there next to a meandering electrical wiring of the flexible circuit foil 64.

FIG. 6 shows a flow diagram of a procedure for positioning and tightening the sensor device according to the embodiments.

In step S110 the sensor electrodes 66 are put at an optimal position of the volar side of the wrist, e.g., as indicated by the measuring positions 110, 120 of FIG. 1. Then, in step S120 the two sides or ends of the wrist strap 62 are wrapped around the wrist, and the signal processing unit 71 of the sensor device is put on top of the wrist. In step S130, the optimal size of the wrist strap for this person is marked, e.g. by adding a mark to the cutting pattern 63 and/or the holes of the strap 62. With a knife or scissor the excess material is removed in step S140. As already mentioned above, separate segments could be provided, as in a necklace. The segments may have a small gap on the inside to allow easy removal: Then, step S140 would be modified to remove excess segments or add missing segments required for the optimum size. On one side the wrist strap 62 is then inserted and fixed in the signal processing unit 71 of the wrist strap 62 in step S150, as shown in FIG. 4. Finally, in step S160, the other side of the wrist strap 62 is fixed onto one or two knobs of the knob-based fixing mechanism 68 after putting the device on the wrist, as shown in FIG. 5. The strap may be made from a rubbery material, which offers a tight, but comfortable fit and stretching ability, so that the sensor device can fir well after fastening.

In summary, the present invention relates to a sensor device and method for tightening and positioning the sensor device with a wristband or strap for a range of wrist sizes and shapes or other body portions, such that the optimal sensor position is obtained and maintained during ambulatory use, which provides two-sided fastening of the strap. The strap has a marker that is positioned by the wearer at a predetermined measuring position, e.g., on the middle of the volar side of the wrist. The wrist is then put on the table to fix its position, and the strap is tightened on both sides of the wrist. This ensures a precision of at least 5 mm of the position of the sensors in the strap.

While the invention has been illustrated and described in detail in the drawings and the foregoing description, such illustration and description are to be considered illustrative or exemplary and not restrictive. The invention is not limited to the disclosed embodiments. From reading the present disclosure, other modifications will be apparent to persons skilled in the art. Such modifications may involve other features which are already known in the art and which may be used instead of or in addition to features already described herein. In particular, other variable fixing mechanisms may be provided at both sides or ends of the strap 62. The sensing device with two-sided fixation of the senor strap may be adapted for measuring skin conductance or other parameters at other body portions, e.g., the ankle(s).

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

Any reference signs in the claims should not be construed as limiting the scope thereof.

The invention claimed is:

1. A sensor device comprising:
   a strap including two adjustable ends;
   two sensors arranged side by side within the strap, the two sensor being configured to measure a physiological parameter at a volar side of a wrist of a human or animal body and spaced apart from each other between approximately 1 mm and 10 mm; and
   a signal processing unit configured to process a measurement output obtained from the two sensors,
   wherein each adjustable end of the strap is structured to be adjustably fixable to the signal processing unit until the two sensors are situated in an optimal location of the volar side of the wrist where a conductive signal value is highest,
   wherein a first adjustable end of the strap includes a segmented pattern that is insertable and fixable to the signal processing unit, the segmented pattern having pieces that are removable and addable,
   wherein a second adjustable end of the strap includes a detachable fixing mechanism of a variable length that is fixable to the signal processing unit, and
   wherein the signal processing unit comprises a user interface structured so that a user or patient wearing the sensor device can monitor and/or control measuring or sensing functions including to assist said user or patient to locate the optimal location of the volar side of the wrist where a conductive signal value is highest.

2. The device according to claim 1, wherein said strap comprises a hollow tunnel for accommodating wiring between the two sensors and said signal processing unit.

3. The device according to claim 1, wherein said signal processing unit comprises a data storage for storing measuring results.

4. The device according to claim 1, wherein said strap comprises at least one marker for positioning the two sensors the location of the volar side of the wrist where the conductive signal value is highest.

5. The device according to claim 4, wherein the location of the volar side of the wrist where the conductive signal value is highest is at a region of the volar side of the wrist where the thumb is located.

6. The device according to claim 1, wherein said strap is adapted to be tightened at both sides of a wrist of said body by at least one of said adjustable fastening and a stretching ability of said strap.

7. The device according to claim 1, wherein said strap comprises at least one recess for accommodating the two sensors.

8. A sensor device comprising: a strap including two adjustable ends; two sensors arranged side by side within the strap, the two sensor being configured to measure a physiological parameter at a volar side of a wrist of a human or animal body and spaced apart from each other between approximately 1 mm and 10 mm; and a signal processing unit configured to process a measurement output obtained from the two sensors, wherein said strap is adapted to be inserted in the signal processing unit at one end of the strap and to be adjustably fixed onto a knob portion of the signal processing unit at the other end of the strap unit until the two sensors are situated in an optimal location of the volar side of the wrist where a conductive signal value is highest, and wherein the signal processing unit comprises a user interface structured so that a user or patient wearing the sensor device can monitor and/or control measuring or sensing functions including to assist said user or patient to locate the optimal location of the volar side of the wrist where a conductive signal value is highest.

9. The device according to claim 8, wherein said strap comprises a hollow tunnel for accommodating wiring between the two sensors and said signal processing unit.

10. The device according to claim 8, wherein said signal processing unit comprises a data storage for storing measuring results.

11. The device according to claim 8, wherein said strap comprises at least one marker for positioning the two sensors the location of the volar side of the wrist where the conductive signal value is highest.

12. The device according to claim 8, wherein the location of the volar side of the wrist where the conductive signal value is highest is at a region of the volar side of the wrist where the thumb is located.

13. The device according to claim 8, wherein said strap is adapted to be tightened at both sides of a wrist of said body by at least one of said adjustable fastening and a stretching ability of said strap.

14. The device according to claim 8, wherein said strap comprises at least one recess for accommodating the two sensors.

15. The device according to claim 8, wherein said one end of said strap comprises a segmented portion with a predetermined segmented pattern for removing or adding strap pieces.

16. A method of tightening and positioning a sensor device to a volar side of a wrist of a human or animal body, said method comprising:
   putting two sensors arranged side by side on a strap of said sensor device at a predetermined position of said body, the two sensors being spaced apart from each other between approximately 1 mm and 10 mm;
   putting a signal processing unit of said sensor device on top of a portion of said body and wrapping the strap around said body portion;
   marking the optimal size of the strap, wherein the size of the strap is optimal when the two sensors are placed on a region of the volar side of the wrist where a conductive signal value is highest;
   removing excess pieces from or adding missing pieces to a segmented pattern at one end of the strap;
   inserting said one end into said signal processing unit and fixing it; and
   fixing the other end of said strap to said signal processing unit by a detachable fixing mechanism with variable length.

\* \* \* \* \*